United States Patent [19]

Moretz et al.

[11] Patent Number: 5,291,617
[45] Date of Patent: Mar. 8, 1994

[54] MOISTURE MANAGEMENT GARMENT

[76] Inventors: Herbert L. Moretz, 20205 Lola Cir., Davidson, N.C. 28036; Daniel L. Brier, 33 angelfish Cay Dr., Key Largo, Fla. 33037

[21] Appl. No.: 945,677

[22] Filed: Sep. 16, 1992

Related U.S. Application Data

[63] Continuation-in-part of Ser. No. 842,224, Feb. 26, 1992, which is a continuation-in-part of Ser. No. 791,066, Nov. 12, 1991, Pat. No. 5,217,782.

[51] Int. Cl.$^5$ .............................................. A41B 9/00
[52] U.S. Cl. .......................................... 2/400; 2/403; 2/405; 2/406; 2/114; 2/53; 2/48; 2/DIG. 11; 2/901; 604/358; 604/378; 604/385.1; 604/393; 604/394; 604/396
[58] Field of Search ...................... 2/49 R, 48, 53, 173, 2/400, 403, 405, 406, 238, 114, DIG. 7, DIG. 11; 604/358, 378, 385.1, 393, 394, 396

[56] References Cited

U.S. PATENT DOCUMENTS

| | | | |
|---|---|---|---|
| 2,166,012 | 7/1939 | La Maida | 2/400 |
| 2,997,044 | 8/1961 | Simons | 2/403 |
| 3,063,452 | 11/1962 | Del Guercio | 604/378 |
| 3,237,625 | 3/1966 | Johnson | 604/378 |
| 3,496,576 | 2/1970 | Artzt | 2/403 |
| 3,838,692 | 10/1974 | Levesque | 604/394 |
| 4,067,068 | 1/1978 | Bregstein et al. | 2/406 |
| 4,573,987 | 3/1986 | Lamb, Jr. | 604/378 |
| 4,585,448 | 4/1986 | Enloe | 604/378 |
| 4,906,243 | 3/1990 | Dravland | 604/394 |

FOREIGN PATENT DOCUMENTS

| | | | |
|---|---|---|---|
| 2608023 | 6/1988 | France | 2/400 |
| 426980 | 4/1935 | United Kingdom | 2/406 |
| 2176692 | 1/1987 | United Kingdom | 2/406 |

*Primary Examiner*—Clifford D. Crowder
*Assistant Examiner*—Gloria Hale
*Attorney, Agent, or Firm*—W. Thad Adams, III

[57] ABSTRACT

A moisture-management garment having a moisture management panel constructed of a moisture management fabric which extends generally between a crotch area of the garment and a waist area of the garment. The moisture management panel includes a first fabric having an inner moisture transport fabric layer constructed of hydrophobic yarns for residing in skin contact during garment wear and an inner dispersal fabric layer constructed of hydrophilic yarns and positioned adjacent to the inner moisture transport layer to receive and disperse moisture transported to it by the inner moisture transport layer. A second fabric is provided having an outer moisture vaporization fabric layer constructed of hydrophobic yarns which is the outermost surface of the moisture management fabric during wear, and an outer moisture dispersal fabric layer constructed of hydrophilic yarns and positioned adjacent to the outer moisture vaporization layer. An intermediate wicking insert is positioned between the first and second fabrics and extends along the garment from the area of the crotch to the area of the waist to wick moisture from the area of the crotch towards the area of the waist of the garment.

25 Claims, 6 Drawing Sheets

MOISTURE MANAGEMENT GARMENT

This application is a continuation-in-part of application Ser. No. 842,224, filed on Feb. 26, 1992, which is a continuation-in-part of application Ser. No. 791,066, filed on Nov. 12, 1991, now U.S. Pat. No. 5,217,782.

TECHNICAL FIELD AND BACKGROUND OF THE INVENTION

This invention relates to garments, particularly undergarments having a crotch area constructed from a moisture management fabric. Examples of such garments are mens' boxer shorts and briefs, pajamas, and womens' panties and similar undergarments. The fabric from which these garments are constructed is intended to quickly move moisture away from the skin of the wearer and slow the outward movement of the moisture while at the same time enhancing the dispersion of the moisture to those fibers of the fabric which do not touch the skin. The fabric also permits gradual migration of moisture in the form of vapor to the outer surface of the fabric in a controlled manner where evaporation will occur. The result of these functions is to keep the skin as dry as possible while preventing outer clothing from becoming wet from the rush of urine through the undergarment from inside to outside. Garments made from this fabric also have novel construction techniques which confine the moisture within the moisture control fabric portions of the garment.

It is important to note that this type of moisture management avoids having to block and hold the moisture against the skin by a thick pad or rubber or plastic shield. Thus, pockets, plastic liners or other additional construction features are unnecessary. This results in a much more comfortable and longer lasting garment, which more closely resembles a conventional undergarment without the novel moisture management features.

Garments constructed in accordance with the invention described in this application may also include different types of athletic apparel. This prevents perspiration-soaked garments next to the skin over a period of time which can cause chafing, irritation and conditions conducive to bacteria, fungus and yeast growth. The garments incorporating panels constructed of the multi-layer fabric are specifically intended to be essentially normal in outer appearance from similar garments without such panels. For this reason the fabric from which the garments according to the invention are constructed uses combinations of fibers which are intended to remove moisture from the area of the skin and disperse the moisture into areas away from the skin in relatively thin layers, rather than concentrating the moisture away from the skin in a relatively small area, as is the case in many disposable urinary incontinence products.

At the same time, the garment permits minor to moderate amounts of liquid to be dispersed without penetrating the garment's outer layer, thus preventing spotting or staining of the garment or of other garments worn over the moisture management garment.

A number of problems must be solved to provide a garment which truly controls moisture in an efficient and hygienic manner. Such a garment should have several back-up layers and structures to progressively hold or disperse moisture. Moreover, the moisture management areas should have some means for preventing migration of moisture from the moisture management areas of the garment into the shell fabric from which the remainder of the garment is constructed. This permits the moisture management portions of the garment to be as small as possible, therefore resulting in a lightweight, comfortable and unobtrusive garment.

Such a garment should also take advantage of the inherent shape of the garment by moving moisture to those areas where dispersion and evaporation can most readily be accomplished, and where penetration of moisture through to the other areas of the garment and to outer clothing is minimized. In general, this involves, as disclosed herein, moving the moisture upwardly towards the waist and away from the crotch area. The waist area has a much greater surface area than the crotch and therefore can accommodate the spreading liquid over a much larger area. Of course, the problem to be solved is how to get the moisture to move upwardly against the pull of gravity. This application addresses the solution to this problem.

SUMMARY OF THE INVENTION

Therefore, it is an object of the invention to provide a moisture management garment such as an undergarment which has portions, such as crotch portions, which are constructed from an integral multi-layer fabric which has moisture management characteristics.

It is another object of the invention to provide a moisture management garment constructed from an integral multi-layer fabric which can be easily fabricated into panels without extensive labor.

It is another object of the invention to provide a moisture management garment constructed of an integral multi-layer fabric which can be incorporated into the crotch area of the garments, such as undergarments, pajamas, athletic apparel and the like.

It is another object of the invention to provide a garment which wicks moisture away from an adjacent body surface.

It is another object of the invention to provide a moisture management garment which is constructed of an integral multi-layer fabric which has adjacent layers of hydrophobic and hydrophilic fabrics which exert a simultaneous push-pull effect on moisture to thereby move the moisture from one side of the adjacent layers to the other side.

It is another object of the invention to provide a moisture-management garment constructed of an integral multi-layer fabric which incorporates one or more layers which are moisture vapor permeable and liquid impermeable.

It is another object of the invention to provide a moisture management garment which has multiple moisture management fabrics which are overlaid and bonded around their peripheries to prevent migration of moisture from moisture management to nonmoisture management areas of the garment.

It is another object to provide a moisture management garment which provides a positive wicking action to pull moisture against the pull of gravity upwardly away from the crotch and towards the waist of the garment where the moisture can more easily be dispersed, thereby promoting quick evaporation.

These and other objects of the present invention are achieved in the preferred embodiments disclosed below by providing a moisture-management garment having a moisture management panel constructed of a moisture management fabric which extends generally between a crotch area of the garment and a waist area of the garment. The moisture management panel includes a first fabric having an inner moisture transport fabric layer constructed of hydrophobic yarns for residing in skin contact during garment wear and an outer dispersal fabric layer constructed of hydrophilic yarns and positioned adjacent to the inner moisture transport layer to receive and disperse moisture transported to it by the inner moisture transport layer.

A second fabric is provided having an outer moisture vaporization fabric layer constructed of hydrophobic yarns which is the outermost surface of the moisture management fabric during wear, and an inner moisture dispersal fabric layer constructed of hydrophilic yarns and positioned adjacent to the outer moisture vaporization layer.

A third fabric having an intermediate wicking insert is positioned between the first and second fabrics and extends along the garment from the area of the crotch to the area of the waist to wick moisture from the area of the crotch towards the area of the waist of the garment.

According to one preferred embodiment of the invention, the wicking insert defines a shape, the width of which generally narrows towards the crotch and widens towards the waist to provide greater surface area and moisture absorption capacity away from the crotch to promote transport of moisture away from the crotch.

According to another preferred embodiment of the invention, the wicking insert is secured to the outer dispersal fabric layer of the first fabric and is not secured to the second fabric.

According to yet another preferred embodiment of the invention, the wicking insert extends from the crotch to the waist of the garment on the front side of the garment.

According to yet another preferred embodiment of the invention, the garment includes first and second wicking inserts, the first of the wicking inserts extending from the crotch to the waist of the garment on the front side, and the second of the wicking inserts extending from the crotch to the waist of the garment on the seat side of the garment.

According to yet another preferred embodiment of the invention, the wicking insert extends from the crotch to the waist of the garment on the seat side of the garment.

According to yet another preferred embodiment of the invention, the garment includes a liquid impermeable vapor permeable moisture management shield in the crotch of the garment. A lowermost portion of the wicking insert overlaps the moisture management shield in surface-to-surface contact with each other to wick moisture away from the moisture management shield and away from the crotch towards the waist of the garment.

A garment intended for athletic wear includes an elastic panel between the waist of the garment and the wicking insert.

Preferably, the wicking insert comprises a generally triangular-shaped upper portion adjacent the waist and a generally elongated lower portion of uniform width.

According to another preferred embodiment of the invention, the wicking insert is generally triangular-shaped.

According to yet another preferred embodiment of the invention, a first wicking insert extends from the crotch to the waist of the garment on the front side and a second wicking insert extends from the crotch to the waist of the garment on the seat side of the garment.

The garment includes a moisture impermeable moisture management panel in the crotch of the garment. A lowermost portion of the first and second wicking inserts overlap the moisture management panel in surface-to-surface contact on opposite ends thereof to wick moisture away from the moisture management panel and away from the crotch towards the waist of the garment on the front and seat sides thereof.

Preferably, the wicking insert includes a plurality of longitudinally-extending and laterally spaced-apart rows of stitching for promoting vertical movement of moisture from the crotch area to the waist area of the garment and thereby discouraging lateral moisture movement.

According to one preferred embodiment of the invention, the wicking insert comprises at least one layer of an absorbent fabric.

According to another preferred embodiment of the invention, the wicking insert comprises at least one layer of cotton flannel.

According to yet another preferred embodiment of the invention, the wicking insert is secured to the inner moisture dispersal fabric layer of the second fabric and is not secured to the first fabric.

According to one preferred embodiment of the invention, the garment includes a liquid impermeable vapor permeable moisture management shield in the crotch of the garment adjacent to the outer moisture vaporization fabric layer of the second fabric. A lowermost portion of the wicking insert overlaps the area of the second fabric covered by the liquid impermeable moisture management shield to wick moisture blocked by the liquid impermeable moisture management shield away from the area of the moisture management shield and away from the crotch towards the waist of the garment.

According to yet another preferred embodiment of the invention, the garment includes a liquid impermeable moisture management shield attached to the inner surface of the second fabric in the crotch area of the garment. A lowermost portion of the wicking insert overlaps the liquid impermeable moisture management shield in surface-to-surface contact with each other to wick moisture away from the moisture management shield and away from the crotch towards the waist of the garment.

According to yet another preferred embodiment of the invention, a first wicking insert extends from the crotch to the waist of the garment on the front side and a second wicking insert extends from the crotch to the waist of the garment on the seat side, the garment including a liquid impermeable moisture management shield in the crotch of the garment. A lowermost portion of the first and second wicking inserts overlap the liquid impermeable moisture management shield in surface-to-surface contact on opposite ends thereof to wick moisture away from the moisture management shield and away from the crotch towards the waist of the garment on the front and seat sides thereof.

According to one preferred embodiment of the invention, a moisture-management garment is provided having a moisture management shield constructed of a moisture management fabric. The moisture management panel extends generally between a crotch area of the garment and a waist area of the garment. The moisture management panel comprises a first fabric having an inner moisture transport fabric layer constructed of hydrophobic yarns and for residing in skin contact during garment wear, and an outer dispersal fabric layer constructed of hydrophilic yarns and positioned adjacent to the inner moisture transport layer to receive and disperse moisture transported to it by the inner moisture transport layer.

A second fabric is provided having an outer moisture vaporization fabric layer constructed of hydrophobic yarns which is the outermost surface of the moisture management fabric during wear, and an inner moisture dispersal fabric layer constructed of hydrophilic yarns and positioned adjacent to the outer moisture vaporization layer.

A third fabric is provided which includes an intermediate wicking insert positioned between the first and second fabrics for extending along the garment from the area of the crotch to the area of the waist to wick moisture from the area of the crotch towards the area of the waist of the garment. The wicking insert includes first and second wicking fabric layers, each of the wicking layers comprising a layer constructed of hydrophilic fibers and a layer constructed of hydrophobic fibers. The hydrophilic layers of the first and second wicking fabric layers are arranged back-to-back to define a moisture transporting channel between the first and second fabrics.

According to another preferred embodiment of the invention, a moisture management garment is provided, having a moisture management panel constructed of a moisture management fabric and extending generally between a crotch area of the garment and a waist area of the garment. The moisture management panel includes a first inner moisture transport fabric layer constructed of hydrophobic yarns for residing in skin contact during garment wear. A second fabric serving as the outer shell of the moisture management panel of the garment is constructed of hydrophobic wicking yarns. A third fabric having an intermediate wicking insert is positioned between the first and second fabrics and extends along the garment from the area of the crotch to the area of the waist to wick moisture from the area of the crotch towards the area of the waist of the garment.

According to various preferred embodiments of the invention, the garment is either men's briefs, men's boxer shorts or women's panties.

According to one preferred embodiment of the invention, the hydrophilic fabric layers are warp-knitted of warp and filling yarns, with the warp yarns oriented in the direction from the crotch to the waist.

According to another preferred embodiment of the invention, the hydrophilic fabric layers are stretch-woven of warp and filling yarns, the warp yarns oriented in the direction from the crotch to the waist.

According to yet another preferred embodiment of the invention, the hydrophobic yarns of the first inner moisture transport fabric are chosen from the group consisting of polyester or polypropylene.

According to yet another preferred embodiment of the invention, the yarns of the second fabric are either polyester, cotton, a blend of polyester and cotton, or a blend of polyester and wool.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
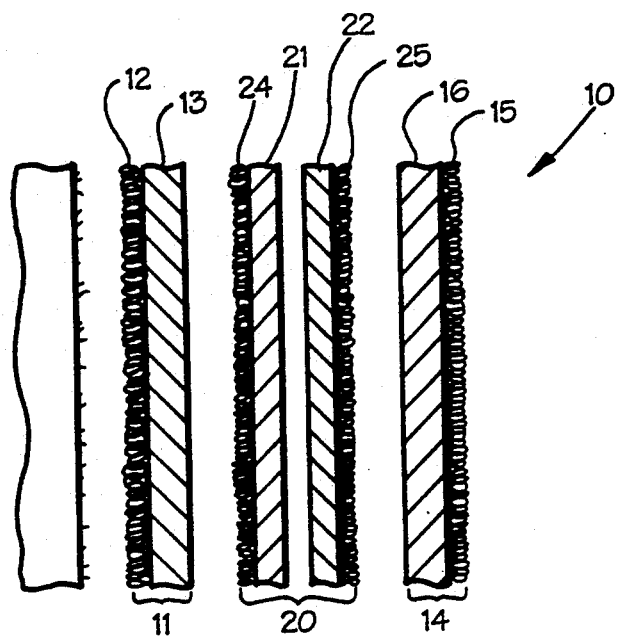
FIG. 1 is a diagrammatic knit construction showing the knit construction of a preferred embodiment of the fabric from which a moisture management garment according to the invention is constructed.

Referring now specifically to the drawings, a moisture management fabric according to a preferred embodiment of the invention is shown in FIG. 1 and broadly indicated at reference numeral 10. The fabric 10 (which is actually very thin, but the thickness of which has been greatly exaggerated for clarity) has a first fabric 11 which includes an inner moisture transport fabric layer 12 which may be constructed of hydrophobic yarns formed from polyester sold by DuPont under the trademarks Coolmax or Thermax, or from generic polyester fibers. The fabric layer 12 is intended to reside in skin contact during garment wear.

An outer dispersal fabric layer 13 is constructed of hydrophilic yarns formed of fibers such as Hydrofil brand fiber sold by Allied Fibers, or cotton, or blends of polyester and cotton. The fabric layer 13 is positioned adjacent to inner moisture transport layer 12 to receive and disperse moisture transported to it by the inner moisture transport layer 12.

A second fabric 14 is provided, and has an outer moisture vaporization fabric layer 15 constructed of hydrophobic yarns as described above, and forms the outermost surface of the moisture management fabric 10, but not necessarily the outer shell of the garment during wear. An inner moisture dispersal fabric layer 16 is constructed of hydrophilic yarns, as described above, and positioned adjacent to the outer moisture vaporization layer 15

A third fabric 20, forming an intermediate wicking insert, is positioned between the first and second fabrics 11 and 14 and is intended to extend along a garment, as described below, from the area of the crotch to the area of the waist to wick moisture from the area of the crotch towards the area of the waist of the garment. Fabric 20 is formed of two hydrophilic fabric layers 21 and 22, which are positioned back-to-back, and two hydrophobic layers 24 and 25 which are positioned on the obverse face of the respective hydrophilic layers 21 and 22. The hydrophobic yarns and hydrophilic yarns from which the layers 21-25 are constructed, are formed of fibers as described above. The adjacent layers 21 and 22 of fabric 20 form between them a channel within which moisture may be transported.

The fabric 10 may be circular or warp knitted, or stretch-woven in accordance with conventional fabric manufacturing techniques. The adjacent fabric layers of each of the fabrics 11, 14 and 20 may be unattached except at the edges where seamed, bonded together by needling, quilting or tack-welding, or integrally-formed together during the fabric formation process. As is explained below, numerous variations based on the above construction are possible. The hydrophilic fabric layers are stretch-woven of warp and filling yarns, the warp yarns are preferably oriented in the direction from the crotch to the waist, since moisture transference is more efficient in the warp direction.

Figure 2:
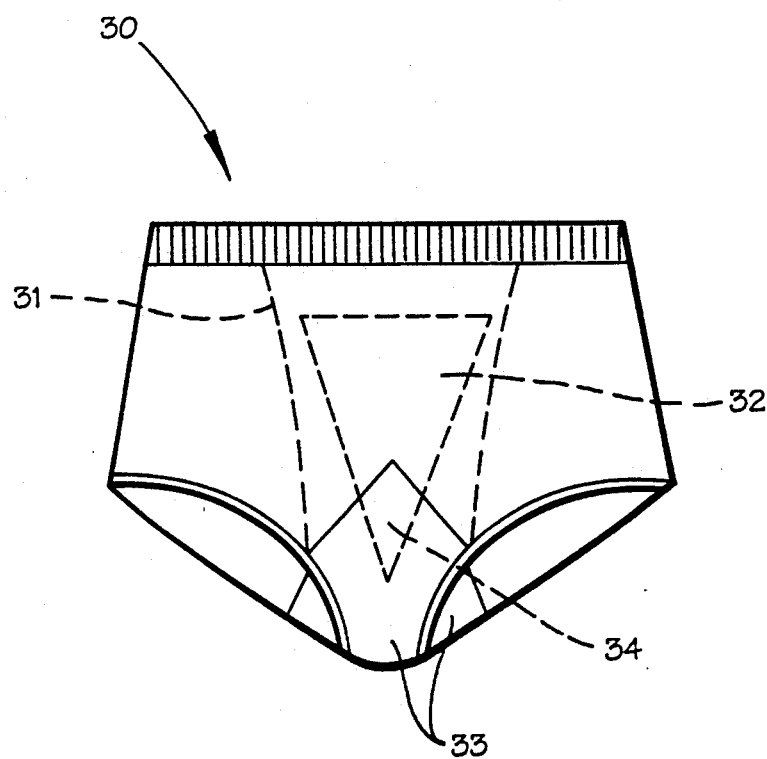
FIG. 2 is a front view of a female undergarment with a moisture management construction according to the present invention.

A garment 30 is shown in FIG. 2. The garment of FIG. 2 is a female panty intended for mild incontinence. The garment 30 is conventionally constructed of conventional material, such as knitted cotton or nylon, to form an outer garment shell. A moisture management panel 31 is sewn into the inside of the garment 30 in the area from the crotch to the area of the waist. The moisture management panel 31 is formed of fabrics 11 and 14, as described above. This fabric combination provides an intense "push-pull" effect which rapidly removes moisture from the vicinity of the skin, dispenses it along the hydrophilic fibers and transports the moisture to the outer surface of the garment 30 where the moisture, dispensed over a wider area, is allowed to more rapidly evaporate.

This effect is further enhanced by providing a wicking insert 32 in the area of greatest moisture concentration. The wicking insert 32 is formed of the fabric 20, described above. The wicking insert 32 is positioned between the fabrics 11 and 14 to form a "sandwich" having a plurality of overlaid layers. Therefore, a cross-section through the center of the moisture management panel 31 of garment 30 from waist to crotch would look like the schematic representation shown in FIG. 1.

Note that the wicking insert 32 is triangular in shape, with the point of the triangle in the area of the crotch, with the base of the triangle positioned just below the waistband. This shape has the effect of permitting the moisture to wick upwardly away from the crotch into an area of the garment more exposed to air and having a greater surface area throughout which the moisture can spread. Thus, in addition to transporting the moisture from the skin to the outside of the garment, the moisture is encouraged by body warmth and capillary action to move up and away from the crotch of the garment 30.

A liquid impervious, vapor permeable crotch shield 33 is sewn into the crotch of the garment 30. A fiber, such as a microdenier fiber, can be used in a dense knit or woven construction for this purpose. Note that the wicking insert 32 and the crotch shield 33 overlap at the area designated 34. The wicking insert is thereby permitted to draw moisture from the liquid impermeable crotch shield 33 area and move it upwardly for evaporation, as described above.

Figure 3:
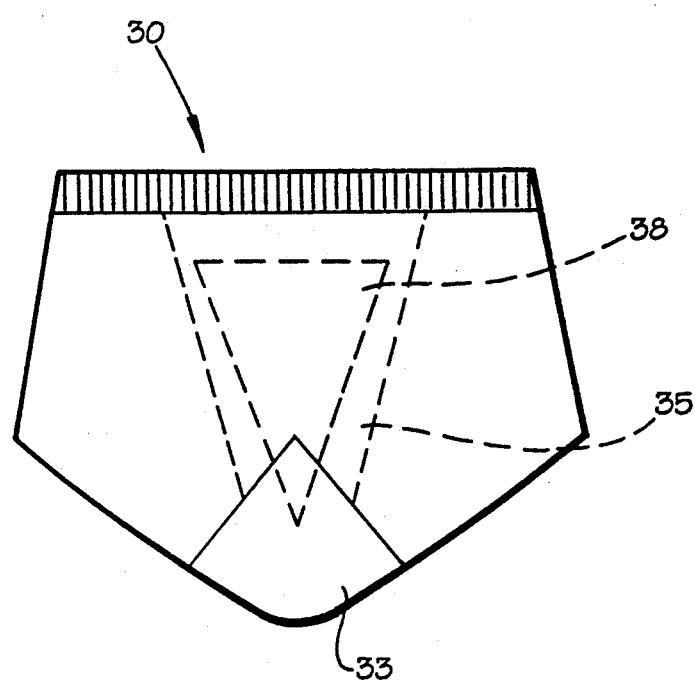
FIG. 3 is a rear view of the female undergarment shown in FIG. 2.

FIG. 3 illustrates the rear of the garment 30, with a moisture management panel 35 constructed of fabrics 11 and 14 as described above sewn into the seat of the garment 30. A wicking insert 38 is sandwiched between fabrics 11 and 14 in the same manner as the wicking insert 32 on the front side of the garment 30 (FIG. 2). Thus, moisture is wicked upwardly towards the waist of the garment 30 in the front and back.

Figure 4:
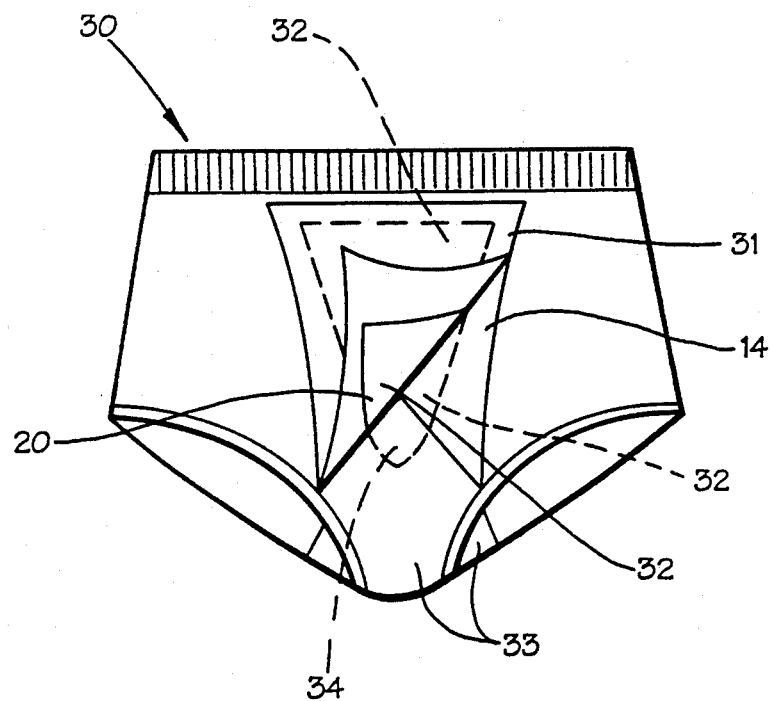
FIG. 4 is a view of the undergarment of FIGS. 2 and 3, turned inside out with elements broken away to show assembly details.

The assembly of the garment 30 is shown in FIG. 4, which shows the garment 30 turned inside out. The "sandwich" assembly of the fabrics 11, 14 and 20 into the moisture management panels 31 and 35, and the wicking inserts 32 and 38 is clearly shown. The crotch shield 33 is sewn to the inside of the outer shell of the garment 30. The area of the wicking insert 32, which is overlapped by the crotch shield 33, is designated 34, and is indicated also by broken lines on the crotch shield 33. The wicking insert 32 and 38 are sewn to the fabric 11, but not to the fabric 14.

Figure 5:
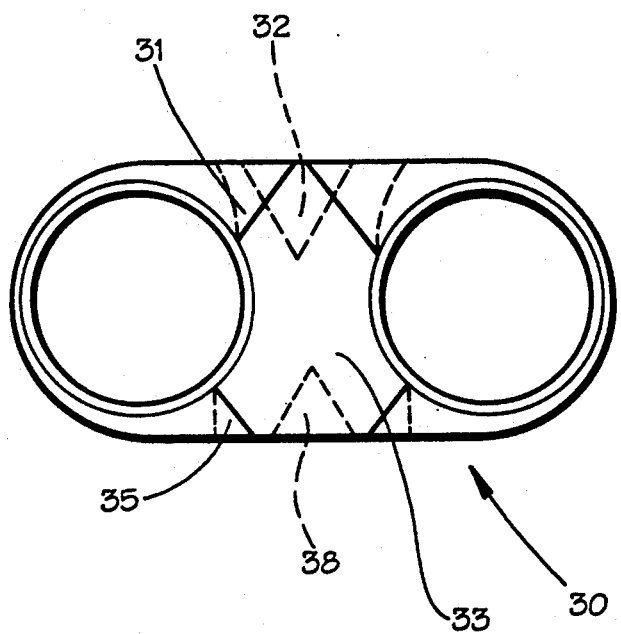
FIG. 5 is a bottom view, looking upwardly, of the garment shown in FIGS. 2, 3 and 4.

A bottom view, looking up, of the garment 30 of FIGS. 2, 3 and 4 is shown in FIG. 5. The garment 30 is indistinguishable from a conventional female panty when viewed from the outside. The selective use of the fiber combinations described above, in combination with the geometry of the garment construction, permits a very effective moisture management garment without any bulky, outwardly visible or disposable components.

Figure 6:
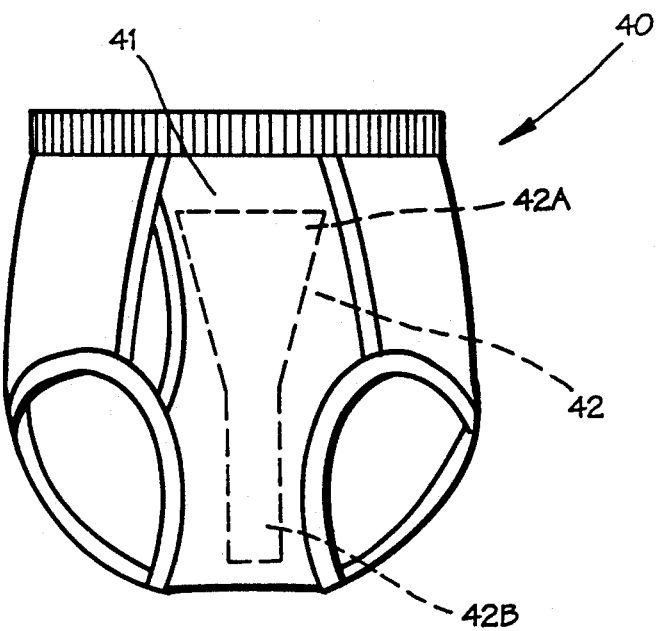
FIG. 6 is a front view of a male undergarment with a moisture management construction according to another embodiment of the invention.

Referring now to FIG. 6, a male brief 40 is shown. The brief 40 is conventionally constructed of combed cotton or cotton/polyester knitted fabric. A moisture management panel 41 comprises the fly panel of the brief 40, and is substituted for a conventional fly panel. The moisture management panel 41 is constructed of overlaid fabrics 11 and 14, described above, with a wicking insert 42 formed of fabric 20 sandwiched between the fabrics 11 and 14.

The wicking insert 42 is shaped into a generally triangular-shaped upper portion 42A adjacent the waist of the garment 40 and a generally elongated lower portion 42B of uniform width which extends downwardly into the crotch area. Moisture released into the crotch area of the garment 40 will be quickly transported from the vicinity of the skin by the hydrophobic fabric layer 12 to the hydrophilic fabric layer 13 of the fabric 11. In areas of the moisture management panel 41 where the wicking insert 42 is not positioned, the moisture is passed by capillary action to the hydrophilic layer 16 of fabric 14. The hydrophobic fabric layer 15 of fabric 14 retards movement of the liquid moisture to the outer surface of the garment 40, but permits and encourages moisture in liquid form to escape and evaporate.

In the area of the wicking insert 42, the moisture is trapped in the fabric layers 24, 21, 22 and 25 of the fabric 20, and is wicked upwardly out of the area of the crotch and into the are of the waist. This wicking action is aided by the relative warmth of the crotch area. Greater surface area near the waist permits the moisture to quickly disperse across the width of the moisture management panel 41 and evaporate. The elongated lower portion 42B of the wicking insert 42 draws moisture away from the leg openings towards the center of the crotch area, and provides a channel for the moisture upwardly away from the crotch and into the waist area. The progressively widening triangular-shaped wicking insert portion 42A spreads the moisture traveling by capillary action upwardly from the crotch area across the width of the moisture management panel 41 in the area of the waist.

Figure 7:
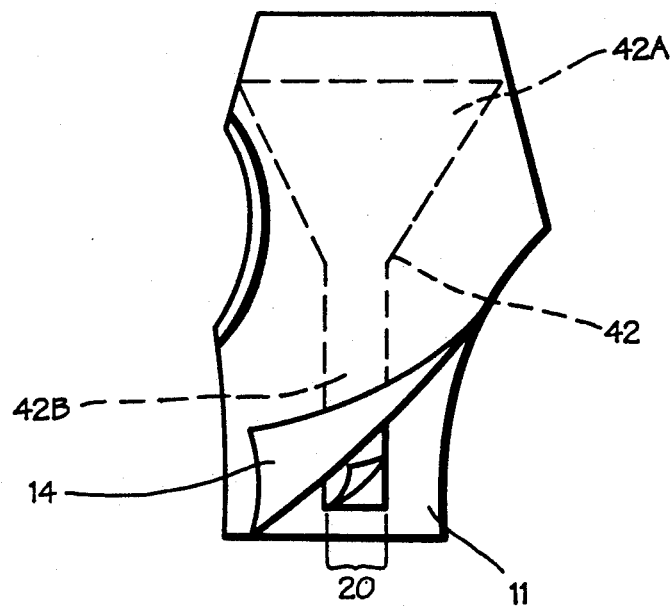
FIG. 7 is a view of the fly panel of the garment in FIG. 6.

The assembly of the moisture management panel 41 is shown in FIG. 7.

Figure 8:
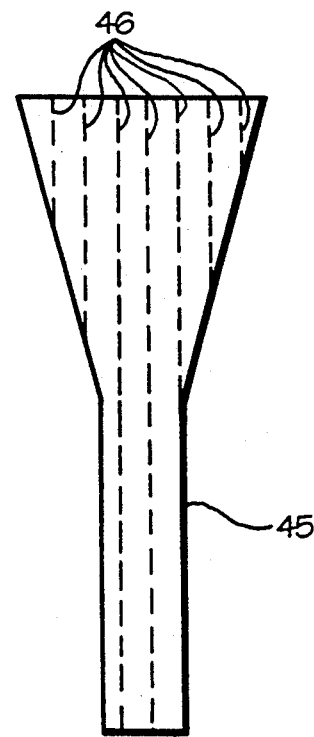
FIG. 8 is a plan view of the front crotch moisture managing wicking insert of the garment shown in FIG. 7.

In accordance with a variation of the invention, a wicking insert 45 as shown in FIG. 8 may be provided which has a spaced-apart series of rows of stitching 46, which extend vertically along the length of the wicking insert 45. The rows of stitching 46 encourage vertical wicking of moisture and thus retard migration of the moisture laterally, thereby reducing spread of the moisture into adjacent, conventionally-constructed areas of the garment. Moisture movement is thereby promoted in the vertical direction towards the waist of the garment. A wicking thread, such as polyester, is preferred.

Figure 9:
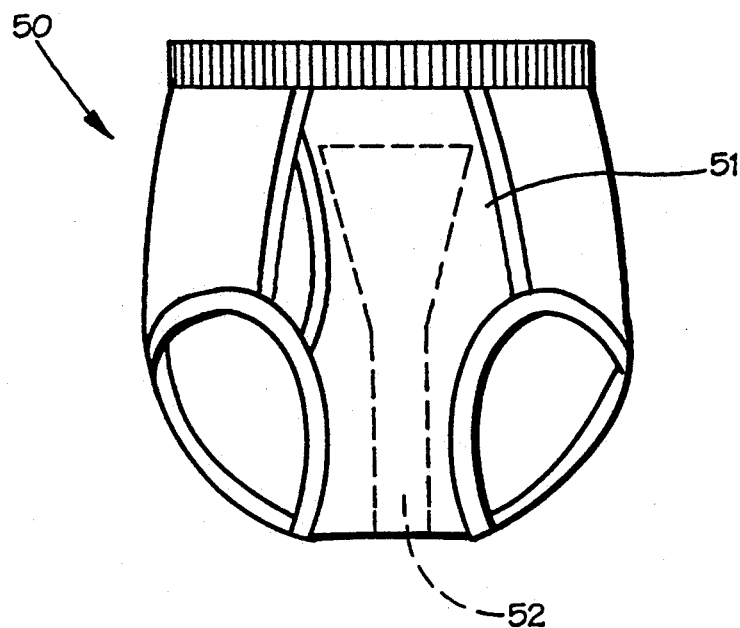
FIG. 9 is a front view of a male undergarment with a wicking insert which extends from front to back.
Figure 11:
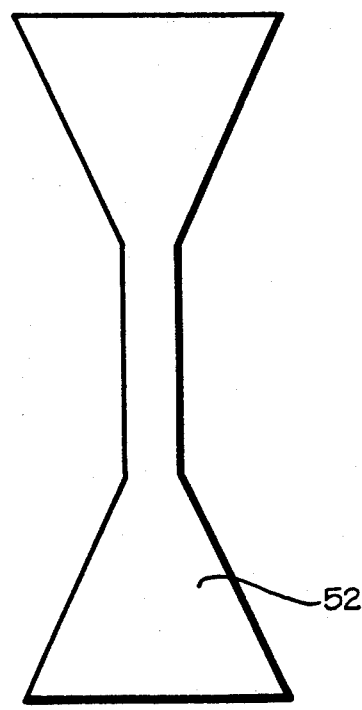
FIG. 11 is a plan view of the wicking insert portion of the crotch area of the garment shown in FIGS. 9 and 10.
Figure 10:
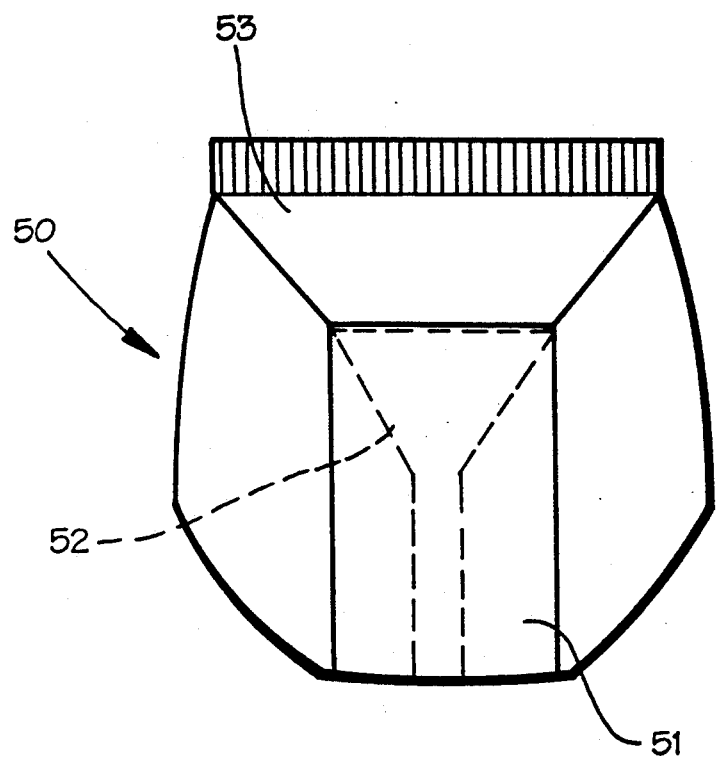
FIG. 10 is a rear view of a male undergarment with a wicking insert which extends from front to back.

Referring now to FIG. 9, a garment 50, also a men's brief, is illustrated. A moisture management panel 51 includes the fly panel portion of the garment 50 and extends through the crotch and up the seat of the garment. As is shown in FIG. 10, a wicking insert 52 is positioned within the moisture management panel 51 and extends from front to back in the manner shown by reference to FIGS. 9 and 10. The moisture management panel 51 and wicking insert 52 are constructed as are the similar constructions of FIGS. 6 and 7 with the exception of the extension into the seat of the garment. This construction provides substantially greater capacity to absorb and manage moisture. For this reason, the garment 50 is particularly useful for instances where greater quantities of moisture must be managed. As is shown in FIG. 10, an elastic panel 53 is sewn into the waistband of the brief 50 and extends down to the upper edge of the moisture management panel 51. The elastic panel may be knitted or stretch woven spandex or a similar product. The elastic panel provides a greater range of movement and greater comfort to the wearer, and is therefore suitable for use as an athletic undergarment. A similarly constructed product could serve as an athletic shorts-type garment, with the particular design and construction of its moisture management features tailored to the particular sport.

A number of variations on the designs set out above are also possible. For example, the wicking insert may be constructed of conventionally woven cotton flannel, and would serve as merely an absorbent panel between the two fabrics 11 and 14.

In all of the embodiments disclosed above, the various fabrics can be treated with an anti-bacterial agent to retard odor and bacteria growth.

Several moisture management garments are described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim

1. A moisture-management garment having a moisture management panel constructed of a moisture management fabric and extending generally between a crotch area of the garment and a waist area of the garment, said moisture management panel comprising:
   (a) a first fabric having an inner moisture transport fabric layer constructed of hydrophobic yarns for residing in skin contact during garment wear, and an outer dispersal fabric layer constructed of hydrophilic yarns and positioned adjacent to said inner moisture transport layer to receive and disperse moisture transported to it by said inner moisture transport layer;
   (b) a second fabric having an outer moisture vaporization fabric layer constructed of hydrophobic yarns and for comprising the outermost surface of the moisture management fabric during wear, and an inner moisture dispersal fabric layer constructed of hydrophilic yarns and positioned adjacent to said outer moisture vaporization layer; and
   (c) a third fabric, comprising an intermediate wicking insert positioned between said first and second fabrics and extending along the garment from the area of the crotch to the area of the waist to wick moisture from the area of the crotch towards the area of the waist of the garment.

2. A moisture management garment according to claim 1, wherein said wicking insert defines a shape, the width of which generally narrows towards the crotch and widens towards the waist to provide greater surface area and moisture absorption capacity away from the crotch to promote transport of moisture away from the crotch without adding unnecessary bulk in the crotch area.

3. A moisture management garment according to claim 1 or 2, wherein the wicking insert is secured to the outer dispersal fabric layer of the first fabric and is separate from the second fabric.

4. A moisture management garment according to claim 1, wherein said wicking insert extends from the crotch to the waist of the garment on a front side of the garment.

5. A moisture management garment according to claim 1, and including first and second wicking inserts, the first of said wicking inserts extending from the crotch to the waist of the garment on a front side and the second of said wicking inserts extending from the crotch to the waist of the garment on a seat side of the garment.

6. A moisture management garment according to claim 1, wherein said wicking insert extends from the crotch to the waist of the garment on a seat side of the garment.

7. A moisture management garment according to claim 1, wherein the garment includes a moisture impermeable moisture management shield in the crotch of the garment, and wherein a lowermost portion of the wicking insert overlaps the moisture management shield in surface-to-surface contact with each other to wick moisture away from the moisture management shield and away from the crotch towards the waist of the garment.

8. A moisture management garment according to claim 6, and including an elastic panel between the waist of the garment and the wicking insert.

9. A moisture management garment according to claim 1, wherein said wicking insert comprises a generally triangular-shaped upper portion adjacent the waist and a generally elongated lower portion of uniform width.

10. A moisture management garment according to claim 1, wherein said wicking insert is generally triangular-shaped.

11. A moisture management garment according to claim 1, wherein a first wicking insert extends from the crotch to the waist of the garment on a front side and a second wicking insert extends from the crotch to the waist of the garment on a seat side of the garment, the garment including a liquid moisture impermeable moisture management shield in the crotch of the garment, and wherein a lowermost portion of the first and second wicking inserts overlap the moisture management shield in surface-to-surface contact on opposite ends thereof to wick moisture away from the moisture management shield and away from the crotch towards the waist of the garment on the front and seat sides thereof.

12. A moisture management garment according to claim 1, wherein said wicking insert includes a plurality of longitudinally-extending and laterally spaced-apart rows of stitching to promote vertical movement of moisture from the crotch area to the waist area of the garment and thereby to discourage lateral moisture movement.

13. A moisture management garment according to claim 1, wherein said wicking insert comprises at least one layer of an absorbent fabric.

14. A moisture management garment according to claim 1, wherein said wicking insert is chosen from the group consisting of at least one layer of cotton flannel, at least one layer of a hydrophilic fabric and at least one layer of synthetic hydrophilic fabric.

15. A moisture management garment according to claim 1, wherein said wicking insert is secured to the inner moisture dispersal fabric layer of the second fabric and is separate from the first fabric.

16. A moisture management garment according to claim 1, wherein the garment includes a liquid impermeable moisture management shield in the crotch of the garment adjacent to the outer moisture vaporization fabric layer of the second fabric, and wherein a lowermost portion of the wicking insert overlaps the area of the second fabric covered by the liquid impermeable moisture management shield to wick moisture blocked by the liquid impermeable moisture management shield away from the area of the moisture management shield and away from the crotch towards the waist of the garment.

17. A moisture management garment according to claim 1, wherein the garment includes a liquid impermeable moisture management shield adjacent to the outer vaporization layer of the second fabric in the crotch area of the garment, and wherein a lowermost portion of the wicking insert overlaps the liquid impermeable moisture management shield in surface-to-surface contact with each other to wick moisture away from the moisture management panel and away from the crotch towards the waist of the garment.

18. A moisture management garment according to claim 1, wherein a first wicking insert extends from the crotch to the waist of the garment on a front side and a second wicking insert extends from the crotch to the waist of the garment on a seat side, the garment including a liquid impermeable moisture management shield in the crotch of the garment, and wherein a lowermost portion of the first and second wicking inserts overlap the liquid impermeable moisture management shield in surface-to-surface contact on opposite ends thereof to wick moisture away from the moisture management shield and away from the crotch towards the waist of the garment on the front and seat sides thereof.

19. A moisture-management garment having a moisture management panel constructed of a moisture management fabric and extending generally between a crotch area of the garment and a waist area of the garment, said moisture management panel comprising:

(a) a first fabric having an inner moisture transport fabric layer constructed of hydrophobic yarns and for residing in skin contact during garment wear, and an outer dispersal fabric layer constructed of hydrophilic yarns and positioned adjacent to said inner moisture transport layer to receive and disperse moisture transported to it by said inner moisture transport layer;

(b) a second fabric having an outer moisture vaporization fabric layer constructed of hydrophobic yarns and for comprising the outermost surface of the moisture management fabric during wear, and an inner moisture dispersal fabric layer constructed of hydrophilic yarns and positioned adjacent to said outer moisture vaporization layer; and (c) a third fabric, comprising an intermediate wicking insert positioned between said first and second fabrics and extending along the garment from the area of the crotch to the area of the waist to wick moisture from the area of the crotch towards the area of the waist of the garment, said wicking insert comprising first and second wicking fabric layers, each of said wicking layers comprising a layer constructed of hydrophilic fibers and a layer constructed of hydrophobic fibers, and the hydrophilic layers of said first and second wicking fabric layers arranged back-to-back to define a moisture transporting channel between said first and second fabrics.

20. A moisture management garment having a moisture management panel constructed of a moisture management fabric and extending generally between a crotch area of the garment and a waist area of the garment, said moisture management panel comprising:

(a) a first inner moisture transport fabric layer constructed of hydrophobic yarns for residing in skin contact during garment wear;

(b) a second fabric comprising the outer shell of the moisture management panel of the garment; and (c) a third fabric comprised of non-absorbent fibers to define an intermediate wicking insert positioned between said first and second fabrics extending along the garment from the area of the crotch to the area of the waist to wick moisture from the area of the crotch towards the area of the waist of the garment.

21. A moisture management garment according to claim 1, 19, or 20, wherein the garment comprises a garment chosen from the group consisting of men's briefs and women's panties.

22. A moisture management garment according to claim 1 or 19, wherein the hydrophilic fabric layers are warp-knitted of warp and filling yarns, with the warp yarns oriented in the direction from the crotch to the waist.

23. A moisture management garment according to claim 1 or 19, wherein the hydrophilic fabric layers are woven of stretch yarns.

24. A moisture management garment according to claim 19 or 20, wherein the hydrophobic yarns of the first inner moisture transport fabric are chosen from the group consisting of polyester or polypropylene.

25. A moisture management garment according to claim 19 or 20, wherein the yarns of the second fabric are chosen from the group consisting of polyester, cotton, a blend of polyester and cotton and a blend of polyester and wool.

* * * * *